(12) United States Patent
Storck et al.

(10) Patent No.: US 7,687,425 B2
(45) Date of Patent: Mar. 30, 2010

(54) THREE-LAYERED OR FOUR-LAYERED CATALYST SYSTEMS FOR PRODUCING PHTHALIC ANHYDRIDE

(75) Inventors: Sebastian Storck, Mannheim (DE); Jürgen Zühlke, Speyer (DE); Samuel Neto, Mannheim (DE); Frank Rosowski, Mannheim (DE)

(73) Assignee: BASF SE, Ludwigshafen (DE)

( * ) Notice: Subject to any disclaimer, the term of this patent is extended or adjusted under 35 U.S.C. 154(b) by 240 days.

(21) Appl. No.: 10/557,993

(22) PCT Filed: May 15, 2004

(86) PCT No.: PCT/EP2004/005247

§ 371 (c)(1),
(2), (4) Date: Nov. 22, 2005

(87) PCT Pub. No.: WO2004/103561

PCT Pub. Date: Dec. 2, 2004

(65) Prior Publication Data

US 2006/0276661 A1    Dec. 7, 2006

(30) Foreign Application Priority Data

May 23, 2003   (DE) ............................... 103 23 818

(51) Int. Cl.
*B01J 31/36* (2006.01)
(52) U.S. Cl. .................................... 502/102
(58) Field of Classification Search ................. 502/102
See application file for complete search history.

(56) References Cited

U.S. PATENT DOCUMENTS

| | | | |
|---|---|---|---|
| 3,799,886 A | 3/1974 | Felice et al. | |
| 3,898,249 A | 8/1975 | Felice et al. | |
| 5,792,719 A | 8/1998 | Eberle et al. | |
| 6,362,345 B1 | 3/2002 | Heidemann et al. | |
| 6,369,240 B1 * | 4/2002 | Hara et al. | 549/249 |
| 6,700,000 B1 * | 3/2004 | Heidemann et al. | 549/248 |
| 2003/0181735 A1 | 9/2003 | Reuter et al. | |

FOREIGN PATENT DOCUMENTS

| | | |
|---|---|---|
| DE | 2 106 796 | 8/1972 |
| DE | 2 238 067 | 2/1974 |
| DE | 196 33 757 A1 | 2/1998 |
| DE | 198 23 262 A1 | 12/1999 |
| DE | 198 23 275 A1 | 12/1999 |
| EP | 0 522 871 A1 | 7/1992 |
| EP | 0 744 214 A1 | 11/1996 |
| EP | 1 063 222 A1 | 12/2000 |
| WO | WO-98/17608 A1 | 4/1998 |
| WO | WO-02/16299 A1 | 2/2002 |
| WO | WO-03/070680 A1 | 8/2003 |

* cited by examiner

*Primary Examiner*—Rebecca L Anderson
*Assistant Examiner*—Shawquia Young
(74) *Attorney, Agent, or Firm*—Connolly Bove Lodge & Hutz LLP

(57) ABSTRACT

Catalyst systems for preparing phthalic anhydride by means of gas-phase oxidation of o-xylene and/or naphthalene, and a process for preparing phthalic anhydride using the catalyst systems.

11 Claims, No Drawings

THREE-LAYERED OR FOUR-LAYERED CATALYST SYSTEMS FOR PRODUCING PHTHALIC ANHYDRIDE

This application is a National Stage of PCT/EP2004/005247 filed May 15,2004, which in turn claims priority from German Application 103 23 818.2, filed May 23, 2003.

The present invention relates to catalyst systems for preparing phthalic anhydride by gas-phase oxidation of o-xylene and/or naphthalene, and also to a process for preparing phthalic anhydride using the catalyst systems.

Phthalic anhydride is prepared industrially by catalytic gas-phase oxidation of o-xylene or naphthalene in shell-and-tube reactors. The starting material is a mixture of a gas comprising molecular oxygen, for example air, and the o-xylene and/or naphthalene to be oxidized. The mixture is passed through a multiplicity of tubes arranged in a reactor (shell-and-tube reactor), in which a bed of at least one catalyst is present. In recent years, it has become normal practice to arrange catalysts of differing activity in zones in the catalyst bed, with the less active catalysts generally being located toward the gas inlet end in the first, uppermost catalyst zone and the more active catalysts being located toward the gas outlet end in the last, bottom-most catalyst zone. This measure enables the activity of the catalyst system in the reactor to be matched to the course of the reaction.

Very different ways of increasing the activity have been described in the prior art, for example:

DE-A-22 38 067 describes the use of two catalyst zones having differing activities. The active compositions differ in their content of potassium ions.

DE-A-198 23 275 describes a two-zone catalyst system. The activities are structured via the amount of active composition on the support and via the amount of added dopants in the form of alkali metal compounds in the active composition (cf. WO 03/70680).

In EP-A 1 063 222, catalyst systems having three or more zones are used and the activity of the individual zones is altered via the amount of phosphorus in the active composition, the amount of active composition on the support ring, the amount of alkali dopant in the active composition and the fill height of the individual catalyst zones in the reaction tube.

WO 98/17608 describes structuring of the activity by means of a differing porosity in the various catalyst zones. The porosity is defined as the free volume between the coated shaped bodies of the bed in the reaction tube.

In the individual catalyst zones, titanium dioxide in the anatase modification is the main constituent of the active composition of the phthalic anhydride catalysts, and serves to support the catalytically active and selective vanadium pentoxide components and other metal oxides.

DE-A 21 06 796 describes the preparation of supported catalysts for the oxidation of o-xylene to phthalic anhydride, in which the titanium dioxide has a BET surface area of from 15 to 100 $m^2/g$, preferably from 25 to 50 $m^2/g$. It is disclosed that mixtures of anatase having a BET surface area of from 7 to 11 $m^2/g$ and titanium dioxide hydrate having a BET surface area of >100 $m^2/g$ are particularly useful, with the components alone not being suitable.

EP-A 744 214 describes a mixture of titanium dioxide having a BET surface area of from 5 to 11 $m^2/g$ and titanium dioxide hydrate having a BET surface area of more than 100 $m^2/g$ in a mixing ratio of from 1:3 to 3:1.

Furthermore, a mixture of titanium dioxides having a BET surface area of from 7 to 11 $m^2/g$ with titanium dioxide hydrate having a BET surface area of >100 $m^2/g$ is described in DE-A 196 33 757. The two components can be present in a weight ratio of from 1:9 to 9:1, based on a gram of $TiO_2$. In addition, a mixture of titanium dioxide with titanium dioxide hydrate in a ratio of 3:1 is described in DE-A 22 38 067.

A problem associated with these mixtures of titanium dioxide with titanium dioxide hydrates is the decrease in the BET surface areas of these mixtures over the life of the catalyst.

EP-A 522 871 describes a relationship between the BET surface area of the titanium dioxide and the catalyst activity. According to this document, the catalyst activity when using titanium dioxide having BET surface areas of less than 10 $m^2/g$ is low. When titanium dioxide having a BET surface area of greater than 60 $m^2/g$ is used, the life of the catalyst is reduced and the phthalic anhydride yield decreases greatly. Preference is given to BET surface areas of from 15 to 40 $m^2/g$.

In multizone catalyst systems, the decrease in activity of the first catalyst zone has an adverse effect on the life of the catalyst. As the catalyst ages, the conversion in the region of the first highly selective zone decreases. Over the operating life of the catalyst, the main reaction zone migrates ever deeper into the catalyst bed, i.e. the o-xylene or naphthalene feed is increasingly reacted only in the subsequent less selective zones. The consequences are reduced phthalic anhydride yields and an increased concentration of by-products or unreacted starting materials. To avoid migration of the main reaction zone into the subsequent zones, the salt bath temperature can be increased continually. However, as the period of operation of the catalysts increases, this measure also leads to a reduction in the phthalic anhydride yield.

The higher the loading of the air with the hydrocarbon to be oxidized, the lower the yield of phthalic anhydride, since a high loading increases the migration of the main reaction zone deeper into the catalyst bed. However, high loadings of from 80 to 120 g/standard $m^3$ are desirable for economical production. A high loading leads to more rapid damage to the catalyst, and thus to shorter operating lives.

It is an object of the present invention to provide a process for preparing phthalic anhydride, which despite a high loading gives phthalic anhydride in high yield and good quality, i.e. in particular with a low phthalide content. Furthermore, the operating life of the catalysts is to be improved.

We have found that this object is achieved by a catalyst system which comprises at least three catalyst zones which are arranged above one another in the reaction tube and whose catalyst activity increases from zone to zone and whose active composition comprises from 70 to 99% by weight of titanium dioxide in the anatase modification, wherein the titanium dioxide (i) in the uppermost zone has a BET surface area of from 5 to 30 $m^2/g$, (ii) in the middle zone or zones has a BET surface area of from 10 to 40 $m^2/g$ and (iii) in the bottom-most zone has a BET surface area of from 15 to 50 $m^2/g$, with the proviso that the BET surface area of the titanium dioxide in the uppermost zone is less than the BET surface area of the titanium dioxide in the middle zone or zones and the BET surface area of the titanium dioxide in the bottom-most zone is greater than the BET surface area of the titanium dioxide in the middle zone or zones.

Furthermore, it has been found that phthalic anhydride can be prepared advantageously using the catalyst system of the present invention.

The catalyst system preferably consists of from three to five zones, in particular four zones. In the case of a three-zone catalyst system, the BET surface area of the titanium dioxides in the anatase modification which are used obeys the following relationship:

$$BET_{zone(i)} < BET_{zone(ii)} < BET_{zone(iii)},$$

in the case of a four-zone catalyst system:

$$BET_{zone(i)} < BET_{zone(iia)} \leq BET_{zone(iib)} < BET_{zone(iii)}$$

and in the case of a five-zone catalyst system:

$$BET_{zone(i)} < BET_{zone(iia)} \leq BET_{zone(iib)} \leq BET_{zone(iic)} < BET_{zone(iii)}.$$

Preference is given to the titanium dioxide
(i) in the uppermost zone having a BET surface area of from 7 to 25 $m^2/g$,
(ii) in the middle zone or zones having a BET surface area of from 10 to 35 $m^2/g$ and
(iii) in the bottom-most zone having a BET surface area of from 15 to 45 $m^2/g$.

In a four-zone catalyst system, the titanium dioxide of the upper middle zone (iia) has, for example, a BET surface area of from 10 to 35 $m^2/g$, in particular from 10 to 30 $m^2/g$, and the titanium dioxide of the lower middle zone (iib) has a BET surface area of from to 40 $m^2/g$, in particular from 15 to 35 $m^2/g$.

In a five-zone catalyst system, the titanium dioxide of the upper middle zone (iia) has, for example, a BET surface area of from 10 to 35 $m^2/g$, in particular from 10 to 30 $m^2/g$, the middle middle zone (iib) has a BET surface area of from 10 to 40 $m^2/g$, in particular from 10 to 35 $m^2/g$, and the lower middle zone (iic) has a BET surface area of from 15 to 40 $m^2/g$, in particular from 15 to 38 $m^2/g$.

The titanium dioxide used in at least one catalyst zone preferably consists of a mixture of titanium dioxides having different BET surface areas. This mixture of titanium dioxide grades comprises, for example, a low surface area titanium dioxide having a BET surface area of advantageously from 5 to 15 $m^2/g$, in particular from 5 to 10 $m^2/g$, and a higher surface area titanium dioxide having a BET surface area of advantageously from 10 to 70 $m^2/g$, in particular from 15 to 50 $m^2/g$. In particular, the titanium dioxide used consists of the two titanium dioxide grades mentioned.

Compared to the titanium oxide hydrates described in the prior art and their mixtures with low surface area $TiO_2$, the mixture used according to the present invention has the advantage that the BET surface area does not change over the operating life of the catalyst of the present invention. A high stability of the activity, i.e. a longer operating life of the catalyst, is thus ensured.

The titanium dioxide used advantageously consists of a mixture of a titanium dioxide having a BET surface area of from 5 to 15 $m^2/g$ and a titanium dioxide having a BET surface area of from 15 to 50 $m^2/g$ in a ratio of
(i) from 1:1.5 to 1:3 in the uppermost zone
(iia) from 1:2 to 1:4 in the upper middle zone
(iib) from 1:2.5 to 1:4 in the lower middle zone and
(iii) from 1:3 to 1:5 in the bottom-most zone.

The bed length of the uppermost catalyst zone (i) is advantageously from 80 to 160 cm, that of the upper middle catalyst zone (iia) is from 20 to 60 cm, that of the lower middle catalyst zone (iib) is from 30 to 100 cm and that of the bottom-most catalyst zone (iii) is from 40 to 90 cm.

Oxidic supported catalysts are suitable as catalysts. To prepare phthalic anhydride by gas-phase oxidation of o-xylene or naphthalene or mixtures thereof, use is generally made of spherical, annular or dish-shaped supports comprising a silicate, silicon carbide, porcelain, aluminum oxide, magnesium oxide, tin dioxide, rutile, aluminum silicate, magnesium silicate (steatite), zirconium silicate or cerium silicate or a mixture thereof. Coated catalysts in which the catalytically active composition is applied in the form of a shell to the support have been found to be particularly useful. The catalytically active constituent is preferably vanadium pentoxide. Furthermore, small amounts of many other oxidic compounds which act as promoters to influence the activity and selectivity of the catalyst, for example by reducing or increasing its activity, can be present in the catalytically active compositions. Such promoters are, for example, alkali metal oxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. Alkali metal oxides act, for example, as promoters which decrease the activity and increase the selectivity. Furthermore, organic binders, preferably copolymers, advantageously in the form of an aqueous dispersion of vinyl acetate-vinyl laurate, vinyl acetate-acrylate, styrene-acrylate, vinyl acetate-maleate, vinyl acetate-ethylene, and also hydroxyethylcellulose can be added to the catalytically active composition, with amounts of binder ranging from 3 to 20% by weight, based on the solids content of the solution of the constituents of the active composition, having been used (EP-A 744 214). Preference is given to using organic binders as described in DE-A 198 24 532. If the catalytically active composition is applied to the support without organic binders, coating temperatures above 150° C. are advantageous. When the abovementioned binders are added, the usable coating temperatures are, depending on the binder used, from 50 to 450° C. (DE-A 21 06 796). The binders applied burn out within a short time after installation of the catalyst and start-up of the reactor. The addition of binder has the additional advantage that the active composition adheres well to the support, so that transport and installation of the catalyst are made easier.

The reaction gas (starting gas mixture) supplied to the catalyst is generally produced by mixing a gas which comprises molecular oxygen and can further comprise suitable reaction moderators such as nitrogen and/or diluents such as steam and/or carbon dioxide in addition to oxygen with the aromatic hydrocarbon to be oxidized. The gas comprising molecular oxygen generally comprises from 1 to 100 mol %, preferably from 2 to 50 mol % and particularly preferably from 10 to 30 mol %, of oxygen, from 0 to 30 mol %, preferably from 0 to 10 mol %, of water vapor and from 0 to 50 mol %, preferably from 0 to 1 mol % of carbon dioxide, balance nitrogen. To produce the reaction gas, the gas comprising molecular oxygen is generally coated with from 30 g to 150 g of the aromatic hydrocarbon to be oxidized per standard $m^3$ of gas, in particular from 60 to 120 g of aromatic hydrocarbon per standard $m^3$.

In multizone catalyst systems, the less active catalyst is generally arranged in the fixed bed so that the reaction gas firstly comes into contact with this catalyst and only subsequently comes into contact with the more active catalyst in the second zone. The reaction gas subsequently comes into contact with the even more active catalyst zones. The catalysts of differing activity can be thermostatted to the same temperature or to different temperatures.

The reaction gas is passed over the prepared catalyst bed at generally from 300 to 450° C., preferably from 320 to 420° C. and particularly preferably from 340 to 400° C. A gauge pressure of generally from 0.1 to 2.5 bar, preferably from 0.3 to 1.5 bar, is advantageously used. The space velocity is generally from 750 to 5000 h$^{-1}$.

The hot spot temperature of the uppermost zone is preferably from 400 to 470° C.; in particular, the maximum temperature is below 450° C. In the middle zone or zones of a multizone catalyst system, the hot spot temperature is advantageously less than 420° C., in particular less than 410° C.

In a preferred embodiment of a three-zone catalyst system, the catalysts have, for example, the following compositions:

for the first, uppermost zone (zone (i)):
 from 7 to 10% by weight of active composition based on the total catalyst, where this active composition comprises:
 from 6 to 11% by weight of vanadium pentoxide,
 from 0 to 3% by weight of antimony trioxide,
 from 0.1 to 1% by weight of an alkali (calculated as alkali metal), in particular cesium oxide,
 and, as balance to 100% by weight, titanium dioxide in the anatase modification having a BET surface area of from 5 to 30 m$^2$/g, for the second, middle zone (zone (ii)):
 from 7 to 12% by weight of active composition based on the total catalyst, where this active composition comprises:
 from 5 to 13% by weight of vanadium pentoxide
 from 0 to 3% by weight of antimony trioxide,
 from 0 to 0.4% by weight of an alkali (calculated as alkali metal), in particular cesium oxide,
 from 0 to 0.4% by weight of phosphorus pentoxide (calculated as P)
 and, as balance to 100% by weight, titanium dioxide in the anatase modification having a BET surface area of from 10 to 40 m$^2$/g, for the third, bottom-most zone (zone (iii)):
 from 8 to 12% by weight of active composition based on the total catalyst, where this active composition comprises:
 from 5 to 30% by weight of vanadium pentoxide
 from 0 to 3% by weight of antimony trioxide,
 from 0 to 0.3% by weight of an alkali (calculated as alkali metal), in particular cesium oxide,
 from 0.05 to 0.4% by weight of phosphorus pentoxide (calculated as P)
 and, as balance to 100% by weight, titanium dioxide, in particular in the anatase modification having a BET surface area of from 15 to 50 m$^2$/g.

In a preferred embodiment of a four-zone catalyst system, the catalysts have, for example, the following compositions:

for the first zone (zone (i)):
 from 7 to 10% by weight of active composition based on the total catalyst, where this active composition comprises:
 from 6 to 11% by weight of vanadium pentoxide,
 from 0 to 3% by weight of antimony trioxide,
 from 0.1 to 1% by weight of an alkali (calculated as alkali metal), in particular cesium oxide,
 and, as balance to 100% by weight, titanium dioxide in the anatase modification having a BET surface area of from 5 to 30 m$^2$/g, for the second zone (zone (iia)):
 from 7 to 12% by weight of active composition based on the total catalyst, where this active composition comprises:
 from 4 to 15% by weight of vanadium pentoxide,
 from 0 to 3% by weight of antimony trioxide,
 from 0.1 to 1% by weight of an alkali (calculated as alkali metal), in particular cesium oxide,
 from 0 to 0.4% by weight of phosphorus pentoxide (calculated as P)
 and, as balance to 100% by weight, titanium dioxide in the anatase modification having a BET surface area of from 10 to 35 m$^2$/g, for the third zone (zone (iib)):
 from 7 to 12% by weight of active composition based on the total catalyst, where this active composition comprises:
 from 5 to 15% by weight of vanadium pentoxide,
 from 0 to 3% by weight of antimony trioxide,
 from 0 to 0.4% by weight of an alkali (calculated as alkali metal), in particular cesium oxide,
 from 0 to 0.4% by weight of phosphorus pentoxide (calculated as P)
 and, as balance to 100% by weight, titanium dioxide in the anatase modification having a BET surface area of from 15 to 40 m$^2$/g, for the fourth zone (zone (iii)):
 from 8 to 12% by weight of active composition based on the total catalyst, where this active composition comprises:
 from 5 to 30% by weight of vanadium pentoxide,
 from 0 to 3% by weight of antimony trioxide,
 from 0.05 to 0.4% by weight of phosphorus pentoxide (calculated as P)
 and, as balance to 100% by weight, titanium dioxide in the anatase modification having a BET surface area of from 15 to 50 m$^2$/g.

If desired, a downstream finishing reactor as described, for example, in DE-A 198 07 018 or DE-A 20 05 969 can also be provided for the preparation of phthalic anhydride. The catalyst used in this reactor is preferably a catalyst which is even more active than the catalyst of the last zone.

The catalyst system of the present invention has made it possible to increase the operating lives as a result of a more uniform distribution of the heat of the reaction over the catalyst bed. Thus, the maximum hot spot temperature is decreased and the phthalic anhydride yield can be increased while maintaining low by-product concentrations.

Phthalic anhydride can be prepared according to the present invention in a high yield and with low concentrations of by-product, in particular phthalide, even at high o-xylene and/or naphthalene loadings, for example from 80 to 120 g/standard m$^3$, and at high space velocities. Under the conditions of the process of the present invention, the phthalide concentration is not higher than 0.05% by weight, based on phthalic anhydride.

EXAMPLES

Catalyst 1: 4 Zones

Upper Zone (i)

29.3 g of anatase (BET surface area 9 m$^2$/g), 69.8 g of anatase (BET surface area=20 m$^2$/g), 7.8 g of V$_2$O$_5$, 1.9 g of Sb$_2$O$_3$, 0.49 g of Cs$_2$CO$_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, external diameter (ED)×length (L)×internal diameter (ID)) by spraying. The weight of the shell of active composition applied was 8% of the total weight of the finished catalyst.

The catalytically active composition applied in this way contained 7.1% by weight of $V_2O_5$, 1.8% by weight of $Sb_2O_3$, 0.36% by weight of Cs after calcination at 400° C. for 4 hours.

The BET surface area of the $TiO_2$ mixture was 16.7 m²/μg.

Upper Middle Zone (iia)

24.6 g of anatase (BET surface area=9 m²/g), 74.5 g of anatase (BET surface area=27 m²/g), 7.8 g of $V_2O_5$, 2.6 g of $Sb_2O_3$, 0.35 g of $Cs_2CO_3$ were suspended in 550 ml of deionized water and stirred for 15 hours. 50 g of an aqueous dispersion (50% by weight) of vinyl acetate and vinyl laurate were subsequently added to the suspension.

The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The catalytically active composition applied in this way contained 7.1% by weight of $V_2O_5$, 2.4% by weight of $Sb_2O_3$, 0.26% by weight of Cs after calcination at 400° C. for 4 hours.

The BET surface area of $TiO_2$ mixture was 22.5 m²/μg.

Lower Middle Zone (iib)

24.8 g of anatase (BET surface area=9 m²/g), 74.5 g of anatase (BET surface area=27 m²/g), 7.8 g of $V_2O_5$, 2.6 g of $Sb_2O_3$, 0.13 g of $Cs_2CO_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The catalytically active composition applied in this way contained 7.1% by weight of $V_2O_5$, 2.4% by weight of $Sb_2O_3$, 0.10% by weight of Cs after calcination at 400° C. for 4 hours.

The BET surface area of $TiO_2$ mixture was 22.5 m²/g.

Lower Zone (iii)

17.2 g of anatase (BET surface area=9 m²/g), 69.1 g of anatase (BET surface area=27 m²/g), 21.9 g of $V_2O_5$, 1.5 g of $NH_4H_2PO_4$ were suspended in 550 ml of deionized water and stirred for 15 hours. 55 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8.0% of the total weight of the finished catalyst.

The catalytically active composition applied in this way contained 20.0% by weight of $V_2O_5$, 0.38% by weight of P after calcination at 400° C. for 4 hours.

The BET surface area of $TiO_2$ mixture was 23.4 m²/g.

Catalyst 2: 4 Zones

Upper Zone (i)

29.3 g of anatase (BET surface area=9 m²/g), 69.8 g of anatase (BET surface area=20 m²/g), 7.8 g of $V_2O_5$, 1.9 g of $Sb_2O_3$, 0.49 g of $Cs_2CO_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The catalytically active composition applied in this way contained 7.1% by weight of $V_2O_5$, 1.8% by weight of $Sb_2O_3$, 0.36% by weight of Cs after calcination at 400° C. for 4 hours.

The BET surface area of the $TiO_2$ mixture was 16.7 m²/g.

Upper Middle Zone (iia)

24.6 g of anatase (BET surface area=9 m²/g), 74.5 g of anatase (BET surface area=20 m²/g), 7.8 g of $V_2O_5$, 2.6 g of $Sb_2O_3$, 0.35 g of $Cs_2CO_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The catalytically active composition applied in this way contained 7.1% by weight of $V_2O_5$, 2.4% by weight of $Sb_2O_3$, 0.26% by weight of Cs after calcination at 400° C. for 4 hours.

The BET surface area of $TiO_2$ mixture was 17.3 m²/g.

Lower Middle Zone (iib)

24.8 g of anatase (BET surface area=9 m²/g), 74.5 g of anatase (BET surface area=20 m²/g), 7.8 g of $V_2O_5$, 2.6 g of $Sb_2O_3$, 0.13 g of $Cs_2CO_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The catalytically active composition applied in this way contained 7.1% by weight of $V_2O_5$, 2.4% by weight of $Sb_2O_3$, 0.10% by weight of Cs after calcination at 400° C. for 4 hours.

The BET surface area of $TiO_2$ mixture was 17.3 m²/g.

Lower Zone (iii)

17.2 g of anatase (BET surface area=9 m²/g), 69.1 g of anatase (BET surface area=27 m²/g), 21.9 g of $V_2O_5$, 1.5 g of $NH_4H_2PO_4$ were suspended in 550 ml of deionized water and stirred for 15 hours. 55 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst. The catalytically active composition applied in this way contained 20.0% by weight of $V_2O_5$, 0.38% by weight of P after calcination at 400° C. for 4 hours. The BET surface area of $TiO_2$ mixture was 23.4 m²/g.

Catalyst 3: 4 Zones (Comparative Example)

Upper Zone (i)

99.5 g of anatase (BET surface area=20 m²/g), 7.8 g of $V_2O_5$, 1.9 g of $Sb_2O_3$, 0.49 g of $Cs_2CO_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The BET surface area of the TiO$_2$ mixture was 20.1 m$^2$/g.

Upper Middle Zone (iia)

99.3 g of anatase (BET surface area=20 m$^2$/g), 7.8 g of V$_2$O$_5$, 2.6 g of Sb$_2$O$_3$, 0.35 g of Cs$_2$CO$_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The BET surface area of the TiO$_2$ mixture was 20.0 m$^2$/g.

Lower Middle Zone (iib)

99.0 g of anatase (BET surface area=20 m$^2$/g), 7.8 g of V$_2$O$_5$, 2.6 g of Sb$_2$O$_3$, 0.13 g of Cs$_2$CO$_3$ were suspended in 550 ml of deionized water and stirred for 15 hours. 50 g of an aqueous dispersion (50% by weight) of vinyl acetate and vinyl laurate were subsequently added to the suspension. The suspension was subsequently applied to 120 g of shaped steatite bodies (magnesium silicate) in the form of rings (7×7×4 mm, ED×L×ID) by spraying. The weight of the shell of active composition applied was 8% of the total weight of the finished catalyst.

The BET surface area of TiO$_2$ mixture was 20.3 m$^2$/g.

Lower Zone (iii)

86.5 g of anatase (BET surface area=20 m$^2$/g), 21.9 g of V$_2$O$_5$, 1.5 g of NH$_4$H$_2$PO$_4$ were suspended in 550 ml of deionized water and stirred for 15 hours. 55 g of an aqueous dispersion (50% by weight) of vinyl acetate and vinyl laurate were subsequently added to the suspension. The suspension was subsequently applied to 1200 g of shaped steatite bodies (magnesium silicate) in the form of rings (7×7×4 mm, ED×L×ID) by spraying. The weight of the shell of active composition applied was 8% of the total weight of the finished catalyst.

The BET surface area of the TiO$_2$ mixture was 20.2 m$^2$/g.

Catalytic Tests:

The tests were carried out in a reactor which had a length of 3.85 m and an internal diameter of 25 mm and was cooled by means of a salt bath. To record a temperature profile, the reactor was equipped with a thermocouple which could be moved over the entire length of the reactor. The thermocouple was kept in a sheath having an external diameter of 2 mm. 4 standard m$^3$ of air laden with from 0 to 100 g of o-xylene (at least 98.5% pure) per standard m$^3$ were passed through the tube hourly. This gave the results summarized below ("PA yield" refers to PA obtained in percent by weight, based on 100% pure o-xylene).

TABLE 1

Results of the catalytic tests

|  | Catalyst 1 | Catalyst 2 | Catalyst 3 Not according to the present invention |
|---|---|---|---|
| Bed length [cm] | 130, 50, 80, 60 | 130, 50, 70, 70 | 130, 50, 70, 70 |
| o-Xylene loading [g/standard m$^3$] | 100 | 100 | 80 |
| Running time [d] | 43 | 40 | 20 |
| SBT [° C.] | 354 | 360 | 347 |
| HST UZ [° C.] | 440 | 440 | 452 |

TABLE 1-continued

Results of the catalytic tests

|  | Catalyst 1 | Catalyst 2 | Catalyst 3 Not according to the present invention |
|---|---|---|---|
| PHD [% by weight] | 0.02 | 0.01 | 0.03 |
| PA yield [% by weight] | 113.5 | 113.7 | 111.3 |

The following abbreviations were used:
HST UZ hot spot temperature in the upper zone
SBT salt bath temperature
PHD phthalide
PA phthalic anhydride

We claim:

1. A catalyst system for preparing phthalic anhydride, which comprises four catalyst layers which are arranged above one another in a reaction tube and whose active composition comprises from 70 to 99% by weight of titanium dioxide in the anatase modification, wherein
   (i) in the uppermost layer the catalyst comprises from 7 to 10% by weight, based on the total catalyst, of active composition comprising from 6 to 11% by weight of V$_2$O$_5$, from 0 to 3% by weight of Sb$_2$O$_3$, from 0.1 to 1% by weight of alkali (calculated as alkali metal) and TiO$_2$ in anatase form having a BET surface area of from 5 to 30 m$^2$/g as balance on support material,
   (ii) in the middle layers the catalyst comprises from 7 to 12% by weight, based on the total catalyst, of active composition comprising from 5 to 13% by weight of V$_2$O$_5$, from 0 to 3% by weight of Sb$_2$O$_3$, from 0 to 0.4% by weight of P, from 0 to 0.4% by weight of alkali (calculated as alkali metal) and TiO$_2$ in anatase form having a BET surface area of from 10 to 40 m$^2$/g as balance on support material,
   (iii) in the bottom-most layer the catalyst comprises from 8 to 12% by weight, based on the total catalyst, of active composition comprising from 5 to 30% by weight of V$_2$O$_5$, from 0 to 3% by weight of Sb$_2$O$_3$, from 0.05 to 0.4% by weight of P, from 0 to 0.3% by weight of alkali (calculated as alkali metal) and TiO$_2$ in anatase form having a BET surface area of from 15 to 50 m$^2$/g as balance on support material,
   with the proviso that the BET surface area of the titanium dioxide in the uppermost layer (i) is less than the BET surface area of the titanium dioxide in the middle layers (ii) and the BET surface area of the titanium dioxide in the bottom-most layer (iii) is greater than the BET surface area of the titanium dioxide in the middle layers, and
   wherein the titanium dioxide in the upper middle layer has a BET surface area of from 10 to 35 m$^2$/g and that in the lower middle layer has a BET surface area of from 15 to 40 m$^2$/g, with the proviso that the BET surface area of the titanium dioxide in the upper middle layer is less than or equal to the BET surface area in the lower middle layer.

2. A catalyst system for preparing phthalic anhydride, which comprises three, four or five catalyst layers which are arranged above one another in a reaction tube and whose active composition comprises from 70 to 99% by weight of titanium dioxide in the anatase modification, wherein
   (i) in the uppermost layer the catalyst comprises from 7 to 10% by weight, based on the total catalyst, of active composition comprising from 6 to 11% by weight of $V_2O_5$, from 0 to 3% by weight of $Sb_2O_3$, from 0.1 to 1% by weight of alkali (calculated as alkali metal) and $TiO_2$ in anatase form having a BET surface area of from 5 to 30% as balance on support material, (ii) in the middle layer or layers the catalyst comprises from 7 to 12% by weight, based on the total catalyst, of active composition comprising from 5 to 13% by weight of $V_2O_5$, from 0 to 3% by weight of $Sb_2O_3$, from 0 to 0.4% by weight of P, from 0 to 0.4% by weight of alkali (calculated as alkali metal) and $TiO_2$ in anatase form having a BET surface area of from 10 to 40 $m^2/g$ as balance on support material, (iii) in the bottom-most layer the catalyst comprises from 8 to 12% by weight, based on the total catalyst, of active composition comprising from 5 to 30% by weight of $V_2O_5$, from 0 to 3% by weight of $Sb_2O_3$, from 0.05 to 0.4% by weight of P, from 0 to 0.3% by weight of alkali (calculated as alkali metal) and $TiO_2$ in anatase form having a BET surface area of from 15 to 50 $m^2/g$ as balance on support material, with the proviso that the BET surface area of the titanium dioxide in the uppermost layer (i) is less than the BET surface area of the titanium dioxide in the middle layer or layers (ii) and the BET surface area of the titanium dioxide in the bottom-most layer (iii) is greater than the BET surface area of the titanium dioxide in the middle layer or layers, wherein the titanium dioxide in at least one catalyst layer consists of a mixture of titanium dioxides having different BET surface areas.

3. The catalyst system according to claim 2, wherein the mixture comprises a titanium dioxide having a BET surface area of from 5 to 15 $m^2/g$ and a titanium dioxide having a BET surface area of from 15 to 50 $m^2/g$ in a ratio of (i) from 1:1.5 to 1:3 in the uppermost layer,
(iia) from 1:2 to 1:4 in the upper middle layer,
(iib) from 1:2.5 to 1:4 in the lower middle layer and
(iii) from 1:3 to 1:5 in the bottom-most layer.

4. A catalyst system for preparing phthalic anhydride, which comprises four catalyst layers which are arranged above one another in a reaction tube and whose active composition comprises from 70 to 99% by weight of titanium dioxide in the anatase modification, wherein (i) in the uppermost layer the catalyst comprises from 7 to 10% by weight, based on the total catalyst, of active composition comprising from 6 to 11% by weight of $V_2O_5$, from 0 to 3% by weight of $Sb_2O_3$, from 0.1 to 1% by weight of alkali (calculated as alkali metal) and $TiO_2$ in anatase form having a BET surface area of from 5 to 30 $m^2/g$ as balance on support material, (ii) in the middle layers the catalyst comprises from 7 to 12% by weight, based on the total catalyst, of active composition comprising from 5 to 13% by weight of $V_2O_5$, from 0 to 3% by weight of $Sb_2O_3$, from 0 to 0.4% by weight of P, from 0 to 0.4% by weight of alkali (calculated as alkali metal) and $TiO_2$ in anatase form having a BET surface area of from 10 to 40 $m^2/g$ as balance on support material, (iii) in the bottom-most layer the catalyst comprises from 8 to 12% by weight, based on the total catalyst, of active composition comprising from 5 to 30% by weight of $V_2O_5$, from 0 to 3% by weight of $Sb_2O_3$, from 0.05 to 0.4% by weight of P, from 0 to 0.3% by weight of alkali (calculated as alkali metal) and $TiO_2$ in anatase form having a BET surface area of from 15 to 50 $m^2/g$ as balance on support material, with the proviso that the BET surface area of the titanium dioxide in the uppermost layer (i) is less than the BET surface area of the titanium dioxide in the middle layers (ii) and the BET surface area of the titanium dioxide in the bottom-most layer (iii) is greater than the BET surface area of the titanium dioxide in the middle layers, wherein a bed length
(i) of the uppermost catalyst layer is from 80 to 160 cm,
(iia) of the upper middle catalyst layer is from 20 to 60 cm,
(iib) of the lower middle catalyst layer is from 30 to 100 cm and
(iii) of the bottom-most catalyst layer is from 40 to 90 cm.

5. A catalyst system for preparing phthalic anhydride, which comprises three, four or five catalyst layers which are arranged above one another in a reaction tube and whose active composition comprises from 70 to 99% by weight of titanium dioxide in the anatase modification, wherein (i) in the uppermost layer the catalyst comprises from 7 to 10% by weight, based on the total catalyst, of active composition comprising from 6 to 11% by weight of $V_2O_5$, from 0 to 3% by weight of $Sb_2O_3$, from 0.1 to 1% by weight of alkali (calculated as alkali metal) and $TiO_2$ in anatase form having a BET surface area of from 5 to 30 $m^2/g$ as balance on support material, (ii) in the middle layer or layers the catalyst comprises from 7 to 12% by weight, based on the total catalyst, of active composition comprising from 5 to 13% by weight of $V_2O_5$, from 0 to 3% by weight of $Sb_2O_3$, from 0 to 0.4% by weight of P, from 0 to 0.4% by weight of alkali (calculated as alkali metal) and $TiO_2$ in anatase form having a BET surface area of from 10 to 40 $m^2/g$ as balance on support material, (iii) in the bottom-most layer the catalyst comprises from 8 to 12% by weight, based on the total catalyst, of active composition comprising from 5 to 30% by weight of $V_2O_5$, from 0 to 3% by weight of $Sb_2O_3$, from 0.05 to 0.4% by weight of P, from 0 to 0.3% by weight of alkali (calculated as alkali metal) and $TiO_2$ in anatase form having a BET surface area of from 15 to 50 $m^2/g$ as balance on support material, with the proviso that the BET surface area of the titanium dioxide in the uppermost layer (i) is less than the BET surface area of the titanium dioxide in the middle layer or layers (ii) and the BET surface area of the titanium dioxide in the bottom-most layer (iii) is greater than the BET surface area of the titanium dioxide in the middle layer or layers, wherein the catalyst activity in the catalyst layers increases from layer to layer, and, wherein the titanium dioxide in at least one catalyst layer consists of a mixture of titanium dioxides having different BET surface areas.

6. A catalyst system for preparing phthalic anhydride, which comprises four catalyst layers which are arranged above one another in a reaction tube and whose active composition comprises from 70 to 99% by weight of titanium dioxide in the anatase modification, wherein (i) in the uppermost layer the catalyst comprises from 7 to 10% by weight, based on the total catalyst, of active composition comprising from 6 to 11% by weight of $V_2O_5$, from 0 to 3% by weight of $Sb_2O_3$, from 0.1 to 1% by weight of alkali (calculated as alkali metal) and $TiO_2$ in anatase form having a BET surface area of from 5 to 30 $m^2/g$ as balance on support material, (ii) in the middle layers the catalyst comprises from 7 to 12% by weight, based on the total catalyst, of active composition comprising from 5 to 13% by weight of $V_2O_5$, from 0 to 3% by weight of $Sb_2O_3$, from 0 to 0.4% by weight of P, from 0 to 0.4% by weight of alkali (calculated as alkali metal) and $TiO_2$ in anatase form having a BET surface area of from 10 to 40 m²/g as balance on support material, (iii) in the bottom-most layer the catalyst comprises from 8 to 12% by weight, based on the total catalyst, of active composition comprising from 5 to 30% by weight of $V_2O_5$, from 0 to 3% by weight of $Sb_2O_3$, from 0.05 to 0.4% by weight of P, from 0 to 0.3% by weight of alkali (calculated as alkali metal) and $TiO_2$ in anatase form having a BET surface area of from 15 to 50 m²/g as balance on support material, with the proviso that the BET surface area of the titanium dioxide in the uppermost layer (i) is less than the BET surface area of the titanium dioxide in the middle layers (ii) and the BET surface area of the titanium dioxide in the bottom-most layer (iii) is greater than the BET surface area of the titanium dioxide in the middle layers, wherein the catalyst activity in the catalyst layers increases from layer to layer, and, wherein a bed length
(i) of the uppermost catalyst layer is from 80 to 160 cm,
(iia) of the upper middle catalyst layer is from 20 to 60 cm,
(iib) of the lower middle catalyst layer is from 30 to 100 cm and
(iii) of the bottom-most catalyst layer is from 40 to 90 cm.

7. A catalyst system for preparing phthalic anhydride, which comprises four catalyst layers which are arranged above one another in a reaction tube and whose active composition comprises from 70 to 99% by weight of titanium dioxide in the anatase modification, wherein (i) in the uppermost layer the catalyst comprises from 7 to 10% by weight, based on the total catalyst, of active composition comprising from 6 to 11% by weight of $V_2O_5$, from 0 to 3% by weight of $Sb_2O_3$, from 0.1 to 1% by weight of alkali (calculated as alkali metal) and $TiO_2$ in anatase form having a BET surface area of from 5 to 30 m²/g as balance on support material, (ii) in the middle layers the catalyst comprises from 7 to 12% by weight, based on the total catalyst, of active composition comprising from 5 to 13% by weight of $V_2O_5$, from 0 to 3% by weight of $Sb_2O_3$, from 0 to 0.4% by weight of P, from 0 to 0.4% by weight of alkali (calculated as alkali metal) and $TiO_2$ in anatase form having a BET surface area of from 10 to 40 m²/g as balance on support material, (iii) in the bottom-most layer the catalyst comprises from 8 to 12% by weight, based on the total catalyst, of active composition comprising from 5 to 30% by weight of $V_2O_5$, from 0 to 3% by weight of $Sb_2O_3$, from 0.05 to 0.4% by weight of P, from 0 to 0.3% by weight of alkali (calculated as alkali metal) and $TiO_2$ in anatase form having a BET surface area of from 15 to 50 m²/g as balance on support material, with the proviso that the BET surface area of the titanium dioxide in the uppermost layer (i) is less than the BET surface area of the titanium dioxide in the middle layers (ii) and the BET surface area of the titanium dioxide in the bottom-most layer (iii) is greater than the BET surface area of the titanium dioxide in the middle layers, wherein the least active catalyst is in the uppermost layer, the next more active catalysts are in the middle layers and the most active catalyst is in the bottom-most layer, and wherein a bed length
(i) of the uppermost catalyst layer is from 80 to 160 cm,
(iia) of the upper middle catalyst layer is from 20 to 60 cm,
(iib) of the lower middle catalyst layer is from 30 to 100 cm and
(iii) of the bottom-most catalyst layer is from 40 to 90 cm.

8. The catalyst system according to claim 1, wherein a bed length
(i) of the uppermost catalyst layer is from 80 to 160 cm,
(iia) of the upper middle catalyst layer is from 20 to 60 cm,
(iib) of the lower middle catalyst layer is from 30 to 100 cm and
(iii) of the bottom-most catalyst layer is from 40 to 90 cm.

9. The catalyst system according to claim 2, wherein a bed length
(i) of the uppermost catalyst layer is from 80 to 160 cm,
(iia) of the upper middle catalyst layer is from 20 to 60 cm,
(iib) of the lower middle catalyst layer is from 30 to 100 cm and
(iii) of the bottom-most catalyst layer is from 40 to 90 cm.

10. The catalyst system according to claim 3, wherein a bed length
(i) of the uppermost catalyst layer is from 80 to 160 cm,
(iia) of the upper middle catalyst layer is from 20 to 60 cm,
(iib) of the lower middle catalyst layer is from 30 to 100 cm and
(iii) of the bottom-most catalyst layer is from 40 to 90 cm.

11. A catalyst system for preparing phthalic anhydride, which comprises four catalyst layers which are arranged above one another in a reaction tube and whose active composition comprises from 70 to 99% by weight of titanium dioxide in the anatase modification, wherein the titanium dioxide in at least one catalyst layer consists of a mixture of titanium dioxides having different BET surface areas, and the mixture comprises a titanium dioxide having a BET surface area of from 5 to 15 m²/g and a titanium dioxide having a BET surface area of from 15 to 50 m²/g in a ratio of (i) from 1:1.5 to 1:3 in the uppermost layer,
(iia) from 1:2 to 1:4 in the upper middle layer,
(iib) from 1:2.5 to 1:4 in the lower middle layer and
(iii) from 1:3 to 1:5 in the bottom-most layer, and wherein (i) in the uppermost layer the catalyst comprises from 7 to 10% by weight, based on the total catalyst, of active composition comprising from 6 to 11% by weight of $V_2O_5$, from 0 to 3% by weight of $Sb_2O_3$, from 0.1 to 1% by weight of alkali (calculated as alkali metal) and $TiO_2$ in anatase form having a BET surface area of from 5 to 30 m²/g as balance on support material, (iia) in the upper middle layer the catalyst comprises from 7 to 12% by weight, based on the total catalyst, of active composition comprising from 4 to 15% by weight of $V_2O_5$, from 0 to 3% by weight of $Sb_2O_3$, from 0.1 to 1% by weight of alkali (calculated as alkali metal), from 0 to .4% by weight of P and $TiO_2$ in anatase form having a BET surface area of from 10 to 35 m²/g as balance on support material, (iib) in the lower middle layer the catalyst comprises from 7 to 12% by weight, based on the total catalyst, of active composition comprising from 5 to 15% by weight of $V_2O_5$, from 0 to 3% by weight of $Sb_2O_3$, from 0 to 0.4% by weight of alkali (calculated as alkali metal), from 0 to .4% by weight of P and TiO$_2$ in anatase form having a BET surface area of from 15 to 40 m$^2$/g as balance on support material, (iii) in the bottom-most layer the catalyst comprises from 8 to 12% by weight, based on the total catalyst, of active composition comprising from 5 to 30% by weight of V$_2$O$_5$, from 0 to 3% by weight of Sb$_2$O$_3$, from 0.05 to 0.4% by weight of P and TiO$_2$ in anatase form having a BET surface area of from 15 to 50 m$^2$/g as balance on support material, with the proviso that the BET surface area of the titanium dioxide in the uppermost layer (i) is less than the BET surface area of the titanium dioxide in the middle layers (ii) and the BET surface area of the titanium dioxide in the bottom-most layer (iii) is greater than the BET surface area of the titanium dioxide in the middle layers.

* * * * *